US009989542B2

(12) United States Patent
Hughes et al.

(10) Patent No.: US 9,989,542 B2
(45) Date of Patent: Jun. 5, 2018

(54) SYSTEMS AND METHODS FOR HEMATOCRIT CORRECTION IN ANALYTE TEST STRIPS

(71) Applicant: Polymer Technology Systems, Inc., Indianapolis, IN (US)

(72) Inventors: Gary L. Hughes, Anderson, IN (US); Robert Huffstodt, Indianapolis, IN (US); Keith Moskowitz, Indianapolis, IN (US)

(73) Assignee: Polymer Technology Systems, Inc., Indianapolis, IN (US)

( * ) Notice: Subject to any disclaimer, the term of this patent is extended or adjusted under 35 U.S.C. 154(b) by 159 days.

(21) Appl. No.: 14/952,015

(22) Filed: Nov. 25, 2015

(65) Prior Publication Data

US 2016/0146845 A1 May 26, 2016

Related U.S. Application Data

(60) Provisional application No. 62/084,351, filed on Nov. 25, 2014.

(51) Int. Cl.

| | |
|---|---|
| ***G01N 33/92*** | (2006.01) |
| ***G01N 33/48*** | (2006.01) |
| ***G01N 33/52*** | (2006.01) |
| ***G01N 33/80*** | (2006.01) |
| ***G01N 33/96*** | (2006.01) |
| ***G01N 21/78*** | (2006.01) |
| ***G01N 27/27*** | (2006.01) |
| ***G01N 27/416*** | (2006.01) |
| ***C12Q 1/60*** | (2006.01) |
| ***G01N 33/49*** | (2006.01) |
| ***G01N 21/84*** | (2006.01) |
| ***G01N 27/327*** | (2006.01) |

(52) U.S. Cl.

CPC ......... *G01N 33/92* (2013.01); *G01N 21/8483* (2013.01); *G01N 27/3274* (2013.01); *G01N 33/492* (2013.01); *G01N 33/80* (2013.01); *C12Q 1/60* (2013.01); *G01N 21/78* (2013.01); *G01N 27/27* (2013.01); *G01N 33/52* (2013.01); *G01N 33/96* (2013.01)

(58) Field of Classification Search

CPC ........ G01N 33/80; G01N 33/92; G01N 33/49; G01N 33/492; G01N 33/96; G01N 33/52; G01N 21/77; G01N 21/78; G01N 21/8483; G01N 27/27; G01N 27/3274; G01N 27/4163; C12Q 1/60

USPC ..... 436/63, 70, 71, 149, 150, 164, 169, 170; 422/420, 421, 422, 423, 82.01, 82.05, 422/82.09; 435/11, 29, 287.1, 288.7

See application file for complete search history.

(56) References Cited

U.S. PATENT DOCUMENTS

| | | | | |
|---|---|---|---|---|
| 8,465,696 | B2 * | 6/2013 | Huffstodt | G01N 21/78 422/68.1 |
| 2005/0003523 | A1 * | 1/2005 | Anaokar | C12Q 1/44 435/287.2 |
| 2011/0155590 | A1 | 6/2011 | Huffstodt et al. | |
| 2013/0084589 | A1 | 4/2013 | Kraft et al. | |
| 2013/0217054 | A1 * | 8/2013 | Huffstodt | G01N 33/66 435/14 |
| 2013/0240375 | A1 * | 9/2013 | Blythe | G01N 27/3274 205/777.5 |
| 2014/0231275 | A1 | 8/2014 | McColl et al. | |
| 2014/0326614 | A1 | 11/2014 | Guthrie et al. | |
| 2016/0091482 | A1 * | 3/2016 | Bauer-Espindola | G01N 27/02 435/11 |

FOREIGN PATENT DOCUMENTS

| | | |
|---|---|---|
| WO | WO 2008/030757 | 3/2008 |
| WO | WO 2012/091728 | 7/2012 |
| WO | WO 2014/140170 | 9/2014 |

OTHER PUBLICATIONS

International Search Report in co-pending PCT Application No. PCT/US2015/062703 dated Feb. 1, 2016 (4 pages).

* cited by examiner

*Primary Examiner* — Maureen Wallenhorst
(74) *Attorney, Agent, or Firm* — Haynes and Boone, LLP

(57) ABSTRACT

A system for determining a level of a lipid analyte corrected for hematocrit includes a test strip configured to receive a sample and a meter configured to receive the test strip. The system further includes circuitry and a microprocessor, the circuitry and microprocessor configured to read the test strip and the sample and determine a level of a lipid analyte and correct the level of the lipid analyte based on a hematocrit level of the sample.

17 Claims, 7 Drawing Sheets

SYSTEMS AND METHODS FOR HEMATOCRIT CORRECTION IN ANALYTE TEST STRIPS

CROSS-REFERENCE TO RELATED APPLICATIONS

This application claims the benefit of Provisional Application No. 62/084,351 filed on Nov. 25, 2014, titled "Systems And Methods For Hematocrit Correction In Analyte Test Strips," the entire disclosure of which is hereby incorporated by reference.

BACKGROUND

Hematocrit is a blood test that measures the percentage of the volume of whole blood that is made up of red blood cells. This measurement depends on the number of red blood cells and the size of red blood cells. The hematocrit (Ht or HcT, British English spelling hematocrit) also is known as packed cell volume (PCV) or erythrocyte volume fraction (EVF). It is normally about 45% for men and 40% for women. As part of detecting many types of blood analytes, a colorimetric testing system is used. In such a test, after isolating the analytes to be measured and reacting the analytes to produce a color change, the reflectance or some other optical measurement is taken. The optical measurement is proportional to the amount of analyte in the sample. In many such calculation schemes, red blood cells are separated from the sample before measurement. This is because the red blood cells affect the color of the color change resulting from the reaction of analytes. The separation of the red blood cells typically is performed using a red blood cell separation layer in the strip, which layer may, for example, be made of a glass fiber matrix. The red blood cells are removed because they would otherwise interfere with the colorimetric test. However, it is difficult, if not impossible, for 100% of the red blood cells to be removed.

In many situations, the occurrence of red blood cells affects the colorimetric test. This negatively affects the accuracy of the test. Although a pre-calculated correction factor can be used in many cases, there are still effects from the red blood cells.

The measurement of low-density lipoprotein (LDL) cholesterol is an important health measurement in the determination of health, especially cardiovascular health. It is desirable to have fast on-site measuring systems for LDL that does not require a laboratory or other facilities. In this way, health professionals may speak with patients immediately after a sample is taken, instead of having to wait days for test results to come back from a lab. In this way, the patient's history and status will be fresh in their mind and, therefore, lead to better results and analysis of patient health.

In the case of the measurement of the concentration of a lipid, such as high density cholesterol (HDL), the test includes placing a drop of blood on a test strip and inserting the test strip in a meter that outputs the result of the test as an electronic signal. The lipid test generally includes a step in which red blood cells are separated from the plasma. The concentration of the lipid then is determined using a colorimetric test. Unfortunately, in many scenarios, the measured concentration may not be reflective of the actual concentration of the lipid (analyte) measured.

BRIEF SUMMARY

In one embodiment, a system for determining a level of a lipid analyte corrected for hematocrit includes a test strip configured to receive a sample and a meter configured to receive the test strip. The system further includes circuitry and a microprocessor, the circuitry and microprocessor configured to read the test strip and the sample and determine a level of a lipid analyte and correct the level of the lipid analyte based on a hematocrit level of the sample. In one alternative, the circuitry and microprocessor are further configured to determine the hematocrit level. In another alternative, the test strip is a hybrid strip. Alternatively, the test strip has a first sample window and a second sample window configured to receive the sample, the first sample window is configured to enable the measurement of the level of lipid analyte, and the second sample window is configured to enable the measurement of hematocrit level. Optionally, the first sample window is an optical sample window. In another alternative, the second sample window is an electrochemical sample window. Optionally, the first sample window includes a spreading layer and is configured to allow for the testing of multiple lipid analytes. In one configuration, the lipid analyte is selected from the group consisting of HDL, LDL, Triglycerides, and total Cholesterol. In another configuration, the meter is configured to receive the test strip and an additional test strip. Optionally, the additional test strip is configured to test for hematocrit. Alternatively, the correction of the level of the lipid analyte is based on correcting the level of the lipid analyte according to an angle of deflection provided by the hematocrit level compared to a normal hematocrit level. Optionally, the Law of Sines is used to determine the amount of correction.

In one embodiment, a method for determining a level of a lipid analyte corrected for hematocrit includes providing a system, the system including: a test strip configured to receive a sample and a meter configured to receive the test strip. The system further includes circuitry and a microprocessor, the circuitry and microprocessor configured to read the test strip and the sample and determine a level of a lipid analyte and correct the level of the lipid analyte based on a hematocrit level of the sample. The method further includes receiving a sample at the test strip and inserting the test strip into the meter. The method further includes the level of the lipid analyte using the circuitry and microprocessor. The method further includes a corrected level of the lipid analyte by correcting for the hematocrit level and providing an output of corrected level of the lipid analyte to a user. Optionally, the method further includes determining, using the circuitry and microprocessor, the hematocrit level in the sample. Alternatively, the level of hematocrit is based on an electrochemical test. Optionally, the level of the lipid analyte is based on an optical test. In one configuration, the test strip is a hybrid strip. In another configuration, the test strip has a first sample window and a second sample window configured to receive the sample, the first sample window is configured to enable the measurement of the level of lipid analyte, and the second sample window is configured to enable the measurement of hematocrit level. Optionally, the first sample window is an optical sample window. Alternatively, the calculating is based on correcting the level of the lipid analyte according to an angle of deflection provided by the hematocrit level compared to a normal hematocrit level. Optionally, the Law of Sines is used to determine the amount of correction.

DETAILED DESCRIPTION OF THE INVENTION

Figure 1:
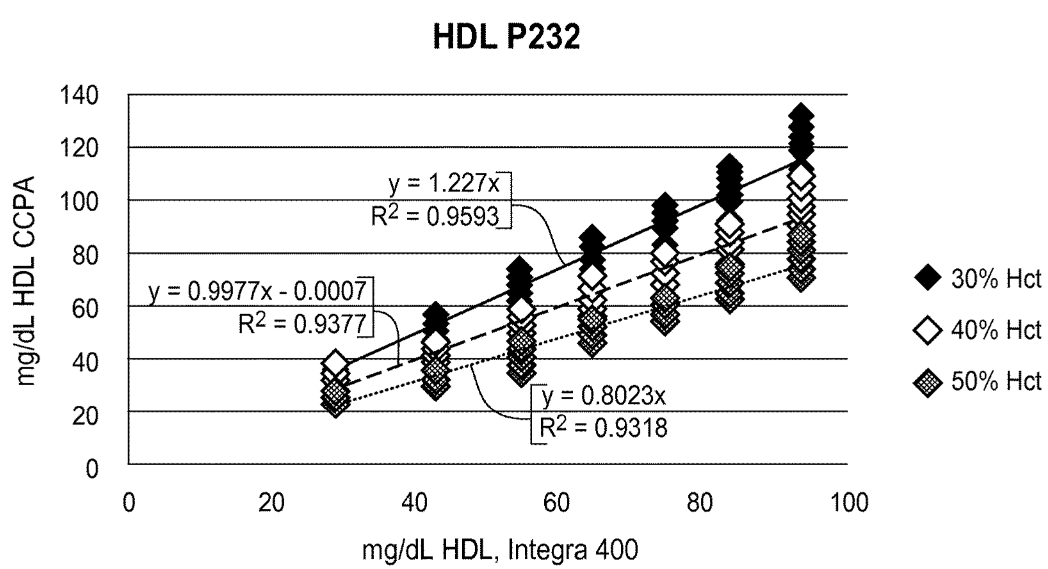
FIG. 1 shows an example of hematocrit bias demonstrated by testing surrogate whole blood samples on a PTS Lipid test strip.

Certain terminology is used herein for convenience only and is not to be taken as a limitation on the embodiments of hematocrit corrected analyte test strips. In the drawings, the same reference letters are employed for designating the same elements throughout the several figures.

Since hematocrit affects the measurement of the color change produced from the reaction of an analyte of interest, it is desirable to accurately compensate for the actual hematocrit level in the sample instead of merely using an estimation of the hematocrit. There is a relationship between the hematocrit level and the result of the colorimetric test. Hematocrit level may also affect electrochemical analysis. Knowledge of this relationship and the hematocrit level results in a more accurate lipid test. Hematocrit usually is measured using a Coulter counter. The output of the Coulter counter is an electronic signal, which signal could be used to automatically adjust the output of the lipid meter.

In many embodiments, a hybrid strip may be created, the hybrid strip allowing for a hematocrit corrected analyte result. An example of such a configuration includes a first sample window, the first sample window receiving a blood sample. The first sample window provides for a vertical flow test strip. The vertical flow test strip may include a vertical stack of layers that provides for the isolation and reaction of a single analyte. In some configurations, the analyte may be total cholesterol, HDL cholesterol, LDL cholesterol, triglycerides, or other analytes. In an alternative configuration, the first window may provide for a multi-analyte measurement. In this configuration, there is a spreading layer that provides spreading of a sample across more than one test stack. In some configurations, this may include a total cholesterol stack, a triglycerides stack, and an HDL or LDL stack.

The stack or stacks of the first sample window may, in some embodiments, include or be sandwiched by electrodes. In this configuration, only a single sample window may be necessary. The electrodes then may be controlled through circuitry and a meter to take readings to determine the hematocrit levels of the sample. In alternative embodiments, a second sample window may be included. This second sample window may be an electrochemical sample window and may merely test for hematocrit. Alternatively, the sample window may test for glucose and hematocrit.

It is thought that a preferred configuration for a test strip might include the use of a tri-panel multi-analyte test that uses a single sample and spreads the sample across three vertical stacks, using a spreading layer, and an electrochemical glucose and hematocrit window that uses another sample. In this configuration, the tri-panel multi-analyte strip may test for a total cholesterol, triglycerides, and an HDL or LDL. Either HDL or LDL may be calculated from the results. Furthermore, the results of these tests may be corrected according to the hematocrit measured in the glucose window. Finally, a glucose result may be generated electrochemically.

Since the most common way of measuring hematocrit is electrochemically, many embodiments of the system will include a combined electrochemical and optical/reflectance meter. By including both systems in the same meter, the meter can automatically and internally apply correction for hematocrit, from one system, electrochemical, to the other, optical.

In many embodiments, the meter includes an algorithm for correcting for hematocrit bias. Alternatively, the algorithm may be implemented in various apparatuses. Various embodiments of systems and methods described herein may be implemented fully or partially in software and/or firmware. This software and/or firmware may take the form of instructions contained in or on a non-transitory computer-readable storage medium. Those instructions then may be read and executed by one or more processors to enable performance of the operations described herein. The instructions may be in any suitable form such as, but not limited to, source code, compiled code, interpreted code, executable code, static code, dynamic code, and the like. Such a computer-readable medium may include any tangible non-transitory medium for storing information in a form readable by one or more computers such as, but not limited to, read only memory (ROM); random access memory (RAM); magnetic disk storage media; optical storage media; a flash memory, etc.

Embodiments of systems and methods described herein may be implemented in a variety of systems including, but not limited to, smartphones, tablets, laptops, and combinations of computing devices and cloud computing resources. For instance, portions of the operations may occur in one device, and other operations may occur at a remote location, such as a remote server or servers. For instance, the collection of the data may occur at a smartphone, and the data analysis may occur at a server or in a cloud computing resource. Any single computing device or combination of computing devices may execute the methods described.

Algorithm for Correcting for Hematocrit Bias

Many point-of-care test strips are plagued by inaccuracy because the test strips have a bias due to hematocrit. Hematocrit is the percentage of red blood cells in the blood. This is a variable that varies from person to person, typically ranging from 30%-55% in the general population. More hematocrit means less plasma available for the diagnostic strip and vice versa. Although the exact reasons for the hematocrit bias have not been determined, it is hypothesized that plasma volume, reflectance of red blood cells, blood enzymes, or pore blockage in membrane-based strips may be factors in hematocrit bias. It is desired to correct for this in the test strip; but when this is not attainable, it is desired to use a mathematical algorithm to offset this bias.

It has been observed through empirical means that diagnostic test strips exhibit a fan-like hematocrit bias pattern. Samples with low hematocrit display over recovery that increases at higher analyte concentrations. In similar fashion, samples with high hematocrit exhibit under recovery that is more pronounced at higher analyte levels. It also appears that this bias is equidistant from the median hematocrit. The difficulty lies in creating an algorithm that will satisfy all hematocrit levels.

FIG. 1 shows an example of the hematocrit bias demonstrated by testing surrogate whole blood samples on a PTS Lipid test strip.

Using the data displayed in FIG. 1, it is possible to create an embodiment of an algorithm to properly adjust for the bias if the hematocrit value is known. The algorithm to correct for hematocrit bias may be agnostic to any diagnostic device. This algorithm may be used with electrochemical test sensors, reflectance test strips, or any other point-of-care device with a hematocrit bias.

The first step in creating this algorithm is to set a curve across the dynamic range of the analyte using blood adjusted to a mean hematocrit. In FIG. 1, 40% hematocrit was chosen for simplicity. Using the same blood, hematocrit adjustments were made to test the extreme ends of the hematocrit range. FIG. 1 shows 30% and 50% because they are the same distance statistically from the normal hematocrit curve. By knowing the slope of the line of the extended hematocrit samples, one can determine the angle between the curves and thereby derive the angle of deflection per percent hematocrit. The angle of deflection per percent hematocrit is a constant that is empirically determined for each point-of-care test. From there, trigonometry principles can be used to adjust the standard value from the meter to a value closer to the truth.

Figure 2:
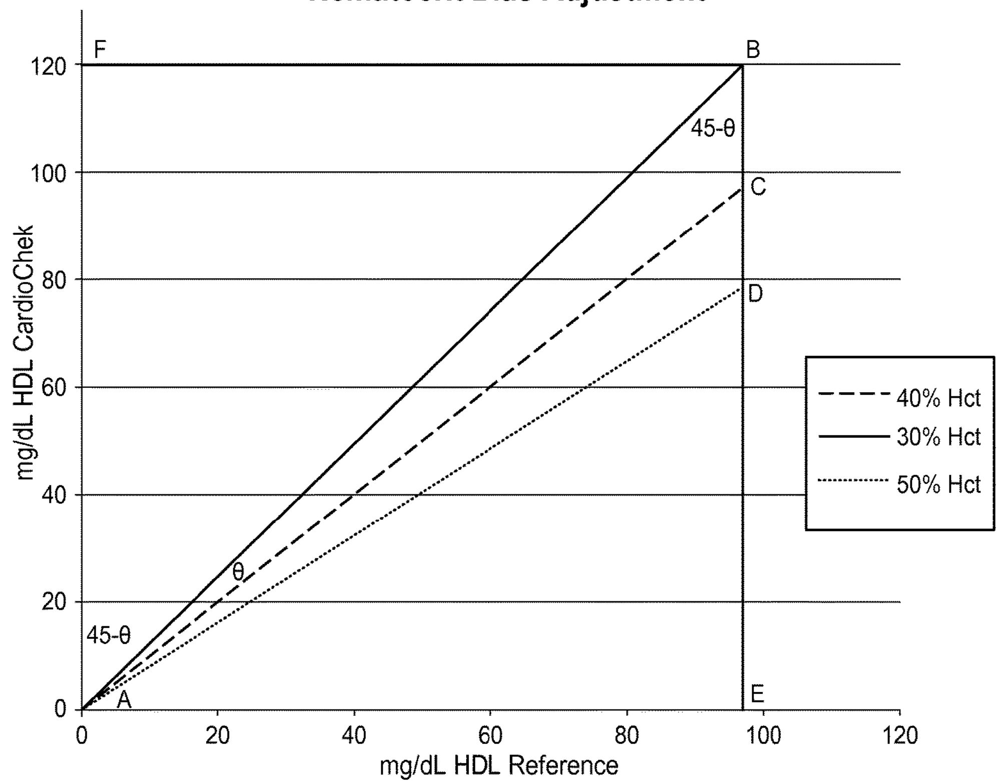
FIG. 2 shows an additional example of a sample having three different hematocrit levels.

FIG. 2 shows an additional example of a sample having three different hematocrit levels. A patient with a hematocrit of 30% and an HDL of 97 will read at 120 mg/dL on the CardioChek® lipid panel. To correct for this, we need to know the distance BC and subtract it from the uncorrected value of 120 mg/dL. It is possible to make these adjustments by applying trigonometry, and in particular using the Law of Sines. The Law of Sines is used to solve non-right triangles when SAA (side-angle-angle) or ASA (angle-side-angle) is known.

Law of Sines $$\frac{\sin A}{a} = \frac{\sin B}{b} = \frac{\sin C}{c}$$

To apply the Law of Sines, it is necessary to solve for a few other parts of ΔABC. We describe below how each part is determined. The equation to be used is $$\frac{\sin\theta}{BC} = \frac{\sin(\text{angle } ACB)}{AB}$$

From previous experimentation, it has been determined that the average angle of deflection per percent hematocrit from 40% is 0.6048 degrees. Knowing that our patient has a 30% hematocrit, then the angle of deflection from normal hematocrit is 6.048 degrees (10×0.6048).

Side AC creates a 45° angle at the origin because the curve is set using this line (y=x).

Side AB can be determined using basic trigonometry. The cos(45−θ)=AF/AB or cos 38.95°=AF/AB. AF is the pre-corrected meter value or 120. Solving for AB then, we get 154.31.

Angle ABC is an alternate interior angle with angle FAE so they are equal. Thus, angle ABC=45−θ.

Angle ACB is now known because we know the other two angles of ΔABC. So angle ACB=180−θ−(45−θ) or 135°. We could also derive this knowing that supplementary angles added together equal 180° and that side AC creates a 45° angle with line EB.

Now we have enough information to apply the Law of Sines to solve for side BC. Using algebra to solve for BC, we get the following:

$$\frac{\sin\theta}{BC} = \frac{\sin(\text{angle } ACB)}{AB}$$

$$BC = \frac{AB(\sin\theta)}{\sin(\text{angle } ACB)}$$

$$BC = 23 \text{ mg/dL}$$

To adjust for the hematocrit, we would subtract 23 from the meter value of 120 to get 97 mg/dL, the reference value.

If the same patient had a 50% hematocrit, then the meter would read 78.4 mg/dL, and we would want to know the distance CD and add it to 78.4 mg/dL. We would again use the Law of Sines to solve for ΔACD and in particular side CD. This method will work for any hematocrit, not just the extremes, because it is based on the angle of deflection from the average hematocrit. In many embodiments, it is built into software to correct for hematocrit bias as we have demonstrated in the following conceptual model.

A Conceptual Model

One of the issues with calibrating strip lots with native blood donors is the variability of the samples from donor to donor. Point-of-Care dry strip chemistries face the added disadvantage of variances in hematocrit that standard hospital chemistry analyzers do not have to deal with. In addition to hematocrit interference, there are other substances such ascorbic acid, bilirubin, uric acid, prescription/non-prescription drugs, etc., that can cause interference on a test strip.

To remove the variability of native blood donors and obtain a larger analyte range, surrogate whole blood was chosen to examine the hematocrit bias in the lipid panel. The surrogate whole blood (SWB) was made with LDL and HDL fractions added back to delipidized serum at a 3:1 ratio. Additionally, glycerol was added to the stock solutions to give added triglyceride readings. Finally, washed "O" red blood cells were added to the "plasma" samples to make 30%, 40%, and 50% hematocrit solutions.

Each sample was tested once across ten CardioChek® meters. The 40% hematocrit samples were used to set the curve and compare the other hematocrit levels. The graphs referenced below illustrate the hematocrit bias in the lipid panel.

Figure 3A:
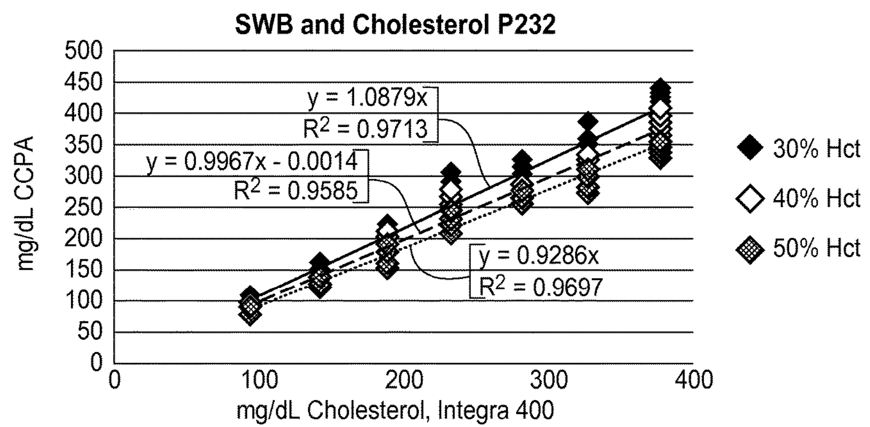
FIGS. 3*a*-3*c* show an example of hematocrit bias displayed across the lipid panel.
Figure 3B:
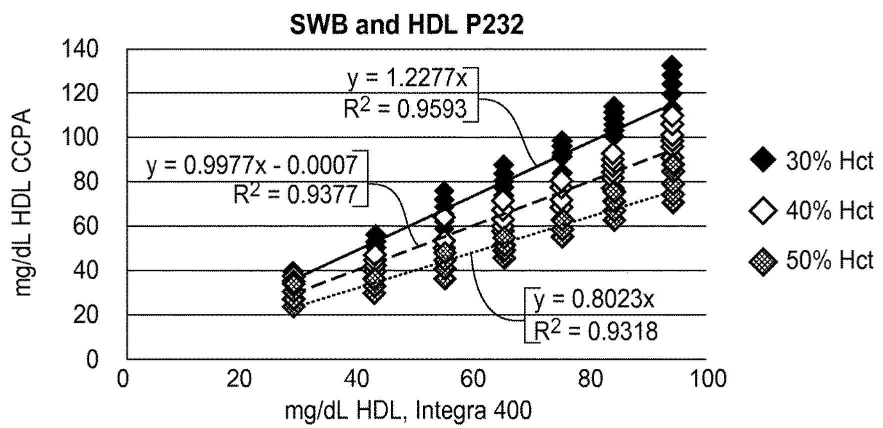
Figure 3C:
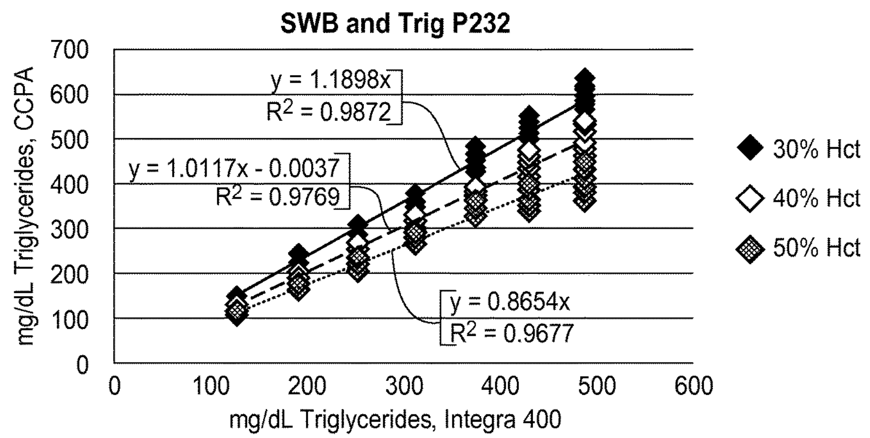

FIGS. 3*a*-3*c* show an example of hematocrit bias displayed across the lipid panel. On the x axis of the graphs, the CardioChek® PA result is shown. This is referenced against the laboratory standard provided by the Integra 400®. The results are shown at three different hematocrit levels of 30%, 40%, and 50%. FIG. 3*a* shows results for total cholesterol, FIG. 3*b* for HDL, and FIG. 3*c* for triyclerides.

Using the algorithm described above, the hematocrit bias can be mathematically corrected as displayed in Table 1 below. The data becomes much tighter with lower total analytical error. This is especially true for HDL and triglycerides.

Figure 4A:
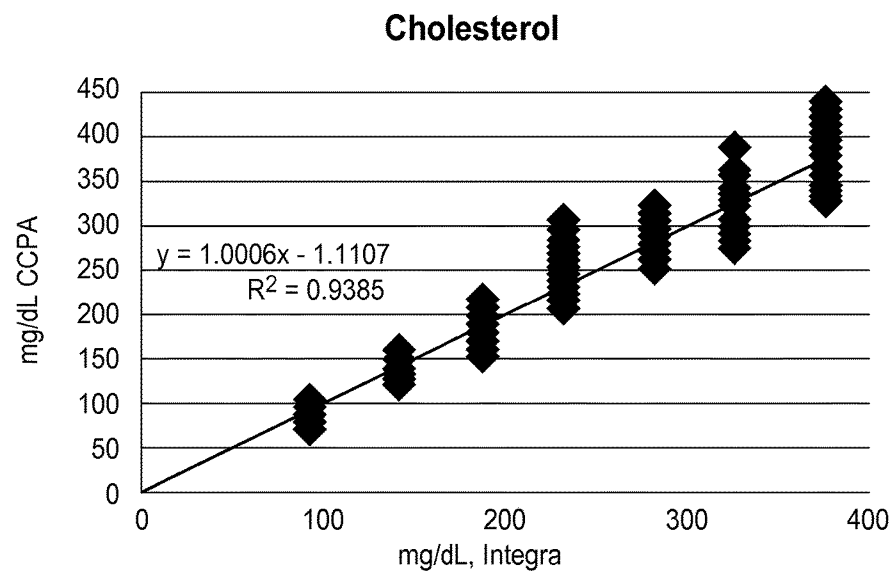
FIGS. 4*a* and 4*b* show exemplary cholesterol readings and cholesterol corrected for hematocrit.
Figure 4B:
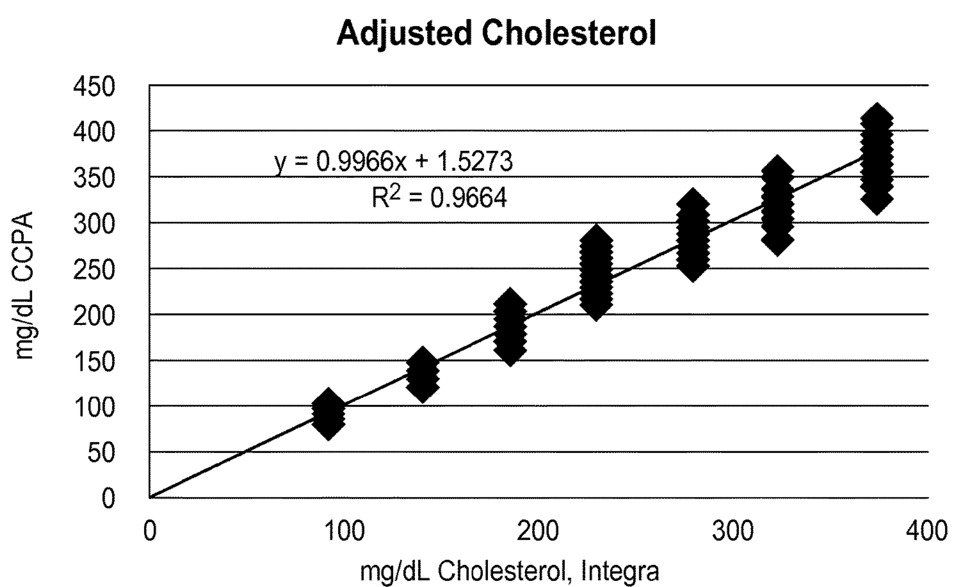
Figure 5A:
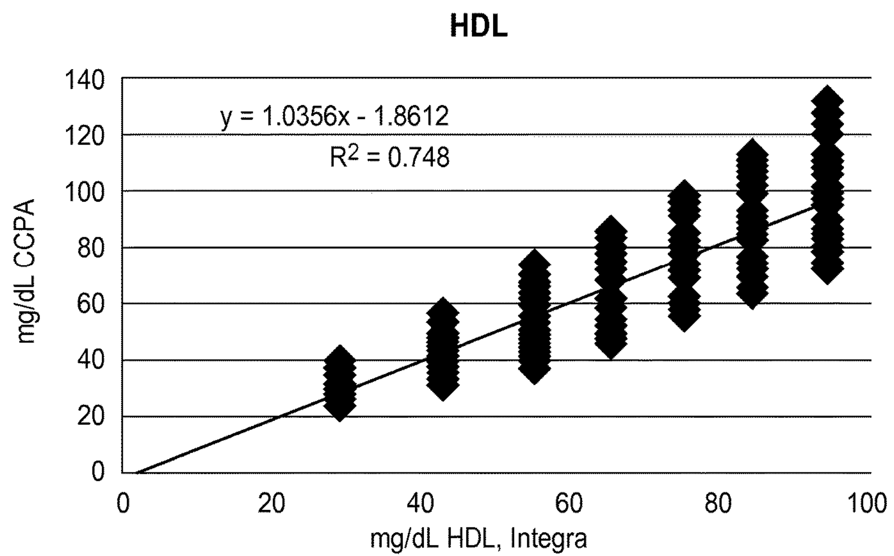
FIGS. 5*a* and 5*b* show exemplary HDL readings and HDL corrected for hematocrit.
Figure 5B:
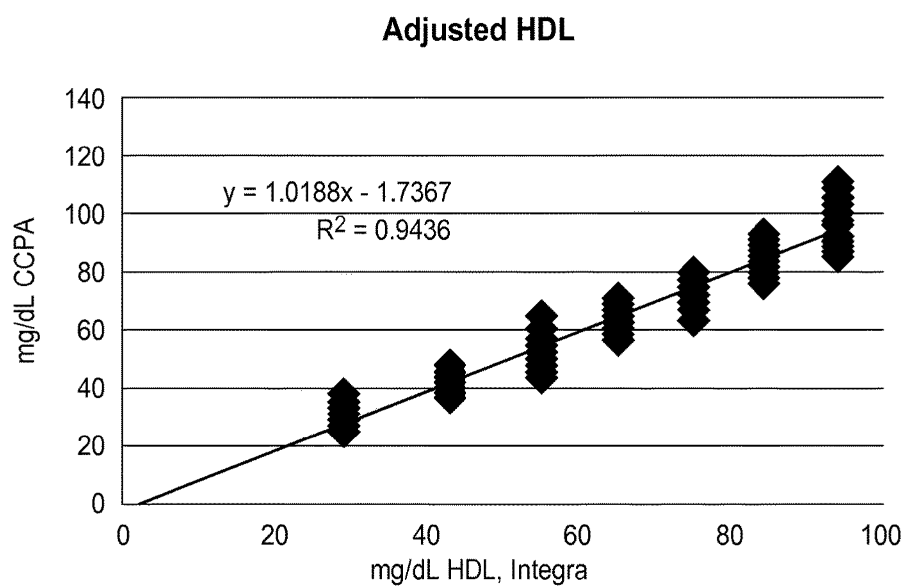
Figure 6A:
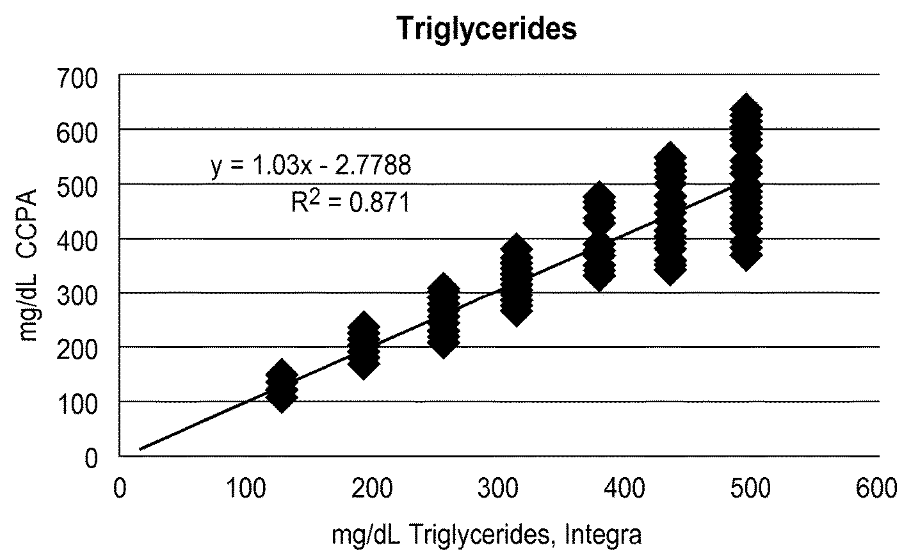
FIGS. 6*a* and 6*b* show exemplary triglyceride readings and triglyceride corrected for hematocrit.
Figure 6B:
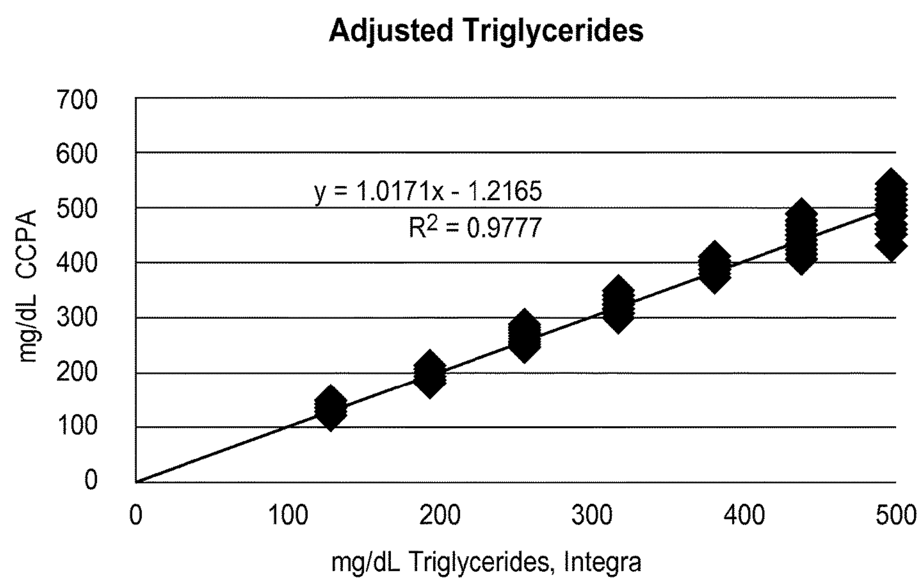

FIGS. 4*a* and 4*b* show exemplary cholesterol readings and cholesterol corrected for hematocrit. FIGS. 5*a* and 5*b* show exemplary HDL readings and HDL corrected for hematocrit. FIGS. 6*a* and 6*b* show exemplary triglyceride readings and triglyceride corrected for hematocrit.

Figure 7A:
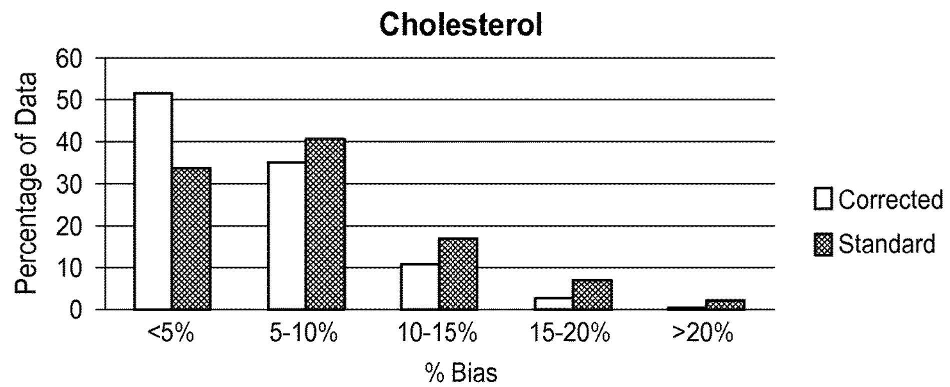
FIGS. 7*a*-7*c* show an example of the benefits of using such a hematocrit algorithm and is further appreciated when one considers the percent bias in a bin analysis.
Figure 7B:
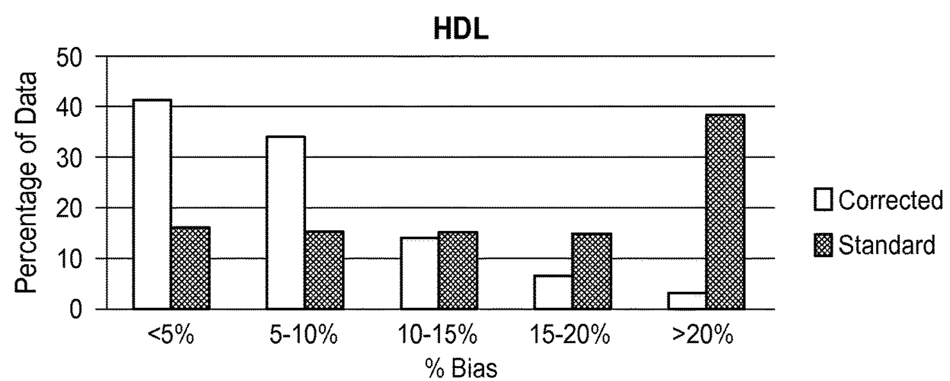
Figure 7C:
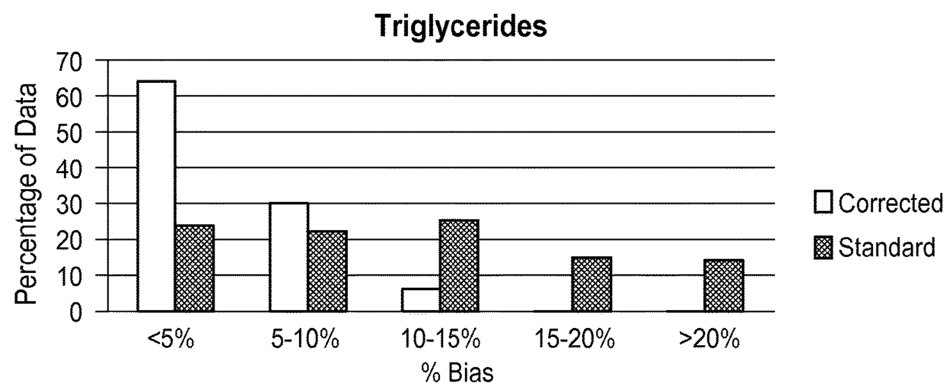

FIGS. 7*a*-7*c* show an example of the benefits of using such a hematocrit algorithm and is further appreciated when one considers the percent bias in a bin analysis. Data is taken from FIGS. 4a-6b. Table 1 shows statistics regarding this data as well.

TABLE 1

| N = 30 across dynamic range | | | |
|---|---|---|---|
| | % Bias (NCEP) | Native Data | HcT Correction Algorithm |
| Chol | 10 | 74.4 | 87 |
| Trig | 15 | 75 | 100 |
| HDL | 12 | 31.4 | 75.7 |

SUMMARY

The embodiments described provide a simple but elegant algorithm to deal with hematocrit bias that plagues many Point-of-Care devices. By knowing the actual hematocrit of the sample, we can mathematically correct for the bias. This correction dramatically improves the accuracy of the test as illustrated above. Another advantage of this algorithm is that it can be used by any Point-of-Care test system that displays a hematocrit bias. The degree of bias from assay to assay will differ, but the mathematical solution remains the same.

While specific embodiments have been described in detail in the foregoing detailed description and illustrated in the accompanying drawings, it will be appreciated by those skilled in the art that various modifications and alternatives to those details could be developed in light of the overall teachings of the disclosure and the broad inventive concepts thereof. It is understood, therefore, that the scope of this disclosure is not limited to the particular examples and implementations disclosed herein but is intended to cover modifications within the spirit and scope thereof as defined by the appended claims and any and all equivalents thereof. Note that, although particular embodiments are shown, features of each attachment may be interchanged between embodiments.

What is claimed as new and desired to be protected by Letters Patent of the United States is:

1. A system for determining a level of a lipid analyte corrected for hematocrit, comprising:

a test strip configured to receive a sample;

a meter configured to receive the test strip; and further including circuitry and a microprocessor located in the meter, the circuitry and microprocessor configured to read the test strip and the sample when the test strip interfaces with the meter and determine a level of a lipid analyte, determine a hematocrit level of the sample, and correct the level of the lipid analyte based on the hematocrit level of the sample, wherein the correction of the level of the lipid analyte is based on correcting the level of the lipid analyte according to an angle of deflection of a line formed by a range of lipid analyte concentrations provided by the hematocrit level compared to said line provided by a normal hematocrit level.

2. The system of claim 1, wherein the test strip is a hybrid strip.

3. The system of claim 2, wherein the test strip has a first sample window and a second sample window configured to receive the sample, the first sample window is configured to enable a measurement of the level of lipid analyte, and the second sample window is configured to enable a measurement of hematocrit level.

4. The system of claim 3, wherein the first sample window is an optical sample window.

5. The system of claim 4, wherein the second sample window is an electrochemical sample window.

6. The system of claim 5, wherein the first sample window includes a spreading layer and is configured to allow for testing of multiple analytes.

7. The system of claim 4, wherein the lipid analyte is selected from the group consisting of HDL, LDL, triglycerides, and total cholesterol.

8. The system of claim 1, wherein the meter is configured to receive the test strip and an additional test strip.

9. The system of claim 8, wherein the additional test strip is configured to test for hematocrit.

10. The system of claim 1, wherein the Law of Sines is used to determine an amount of correction.

11. A method for determining a level of a lipid analyte corrected for hematocrit, comprising:

providing a system, the system including:

a test strip configured to receive a sample;

a meter configured to receive the test strip; and further including circuitry and a microprocessor located in the meter, the circuitry and microprocessor configured to read the test strip and the sample when the test strip interfaces with the meter, determine a hematocrit level of the sample, and determine a level of a lipid analyte and correct the level of the lipid analyte based on the hematocrit level of the sample;

receiving a sample at the test strip and inserting the test strip into the meter;

determining the level of the lipid analyte and the hematocrit level using the circuitry and microprocessor;

calculating a corrected level of the lipid analyte by correcting for the hematocrit level; and providing an output of corrected level of the lipid analyte to a user, wherein the calculating is based on correcting the level of the lipid analyte according to an angle of deflection of a line formed by a range of lipid analyte concentrations provided by the hematocrit level compared to said line provided by a normal hematocrit level.

12. The method of claim 11, wherein the level of hematocrit is based on an electrochemical test.

13. The method of claim 12, wherein the test strip is a hybrid strip.

14. The method of claim 13, wherein the test strip has a first sample window and a second sample window configured to receive the sample, the first sample window is configured to enable a measurement of the level of lipid analyte, and the second sample window is configured to enable a measurement of hematocrit level.

15. The method of claim 14, wherein the first sample window is an optical sample window.

16. The method of claim 11, wherein the level of the lipid analyte is based on an optical test.

17. The method of claim 11, wherein the Law of Sines is used to determine an amount of correction.

* * * * *